United States Patent [19]

Constantinescu

[11] Patent Number: 4,510,925
[45] Date of Patent: Apr. 16, 1985

[54] METHOD AND APPARATUS FOR TREATING A LIVING BODY

[75] Inventor: Dan Constantinescu, 60 rue des Mathurins, Paris, France, 75008

[73] Assignee: Dan Constantinescu, Paris, France

[21] Appl. No.: 481,153

[22] Filed: Apr. 1, 1983

Related U.S. Application Data

[63] Continuation of Ser. No. 300,690, Sep. 9, 1981, abandoned, which is a continuation of Ser. No. 038,943, May 14, 1979, abandoned.

[30] Foreign Application Priority Data

May 17, 1978 [FR] France .................................. 78 14615

[51] Int. Cl.³ .................................................. A61N 1/42
[52] U.S. Cl. ....................................................... 128/1.3
[58] Field of Search ............................ 128/1.3–1.5, 128/421–422, 804

[56] References Cited

U.S. PATENT DOCUMENTS

| 647,687 | 4/1900 | Topham | 128/1.3 |
|---|---|---|---|
| 1,418,903 | 6/1922 | Benson | 128/1.5 |
| 1,615,295 | 1/1927 | Von Hutschler | 128/1.5 |
| 1,724,439 | 8/1929 | Von Hutschler | 128/1.5 |
| 2,567,757 | 9/1951 | Argento | 128/804 |
| 3,169,524 | 2/1965 | Langevin | 128/200.21 |
| 3,194,236 | 7/1965 | Wehner | 128/202.25 |
| 3,246,159 | 4/1966 | Pankove | 350/1.2 |
| 3,280,816 | 10/1966 | Priore | 128/1.3 |
| 3,337,776 | 8/1967 | Elmi | 361/143 |

FOREIGN PATENT DOCUMENTS

| 143715 | 8/1903 | Fed. Rep. of Germany | 128/1.3 |
|---|---|---|---|
| 2116869 | 10/1971 | Fed. Rep. of Germany | 128/1.3 |
| 2353959 | 5/1975 | Fed. Rep. of Germany | 128/1.3 |
| 1573153 | 7/1969 | France | 128/1.3 |
| 2210420 | 7/1974 | France | 128/1.3 |
| 2291773 | 11/1974 | France | 128/1.3 |
| 2365911 | 4/1978 | France | 128/1.3 |
| 305664 | 2/1933 | Italy | 128/1.3 |
| 592479 | 5/1959 | Italy | 128/1.3 |
| 741651 | 12/1955 | United Kingdom | 128/1.3 |
| 491390 | 2/1976 | U.S.S.R. | 128/1.3 |

*Primary Examiner*—Kyle L. Howell
*Assistant Examiner*—Francis J. Jaworski
*Attorney, Agent, or Firm*—Lewis H. Eslinger

[57] ABSTRACT

The present invention relates, on the one hand, to a therapeutic method consisting in transmitting magnetic signals to a living substratum or body which signals have informational significance compatible with the informational organization and the automatic regulation of the substratum in order to act on its functional behavior to balance or dynamize it, and on the other hand, to an apparatus for transmitting said signals. Each signal is formed by a sequence of magnetic fields generated by selectively coupling an electrical signal into like and dissimilar magnetic poles to define a wave train of selected form, the wave train being repeated at least three times, the basic frequency of the magnetic waves being of the order of 40 to 80 KHz, and the signal duration being of the order of 100 to 200 microseconds.

10 Claims, 6 Drawing Figures

METHOD AND APPARATUS FOR TREATING A LIVING BODY

This is a continuation of application Ser. No. 300,690, filed Sept. 9, 1981, which is a continuation of application Ser. No. 038,943, filed May 14, 1979 both abandoned.

BACKGROUND OF THE INVENTION

The present invention relates to a method and apparatus for the treatment of a living substratum or body whereby magnetic signals compatible with the informational organization and the automatic regulation of the living organisms are transmitted so as to be received by the organism and to bring about responses therein of functional equilibration and dynamization.

So far, electromagnetotherapy has, in its various aspects, been applied to living organisms to cause direct physical action therein. Thus, high frequency electrotherapy and conventional electromagnetotherapy traditionally base their action on warming the tissues deep beneath the surface due to the absorption of the electromagnetic energy which is converted into heat according to Joule's law. Pulsed, high frequency electromagnetotherapy appears to cause conversion a piezoelectric mechanism in the crystalline structures of the tissues, thus explaining its thermal effects. Low frequency electrotherapy, and low frequency electromagnetotherapy, causes ionic inductions and dissociations in the living tissues.

SUMMARY OF THE INVENTION

Another mode of action of electromagnetic fields on living organisms should also be considered: the informational signals organisms use for automatic regulation of the living system for equilibration and adaptation.

Recently biocybernetics has shown that living regulator systems use such signals on all levels of operation of the organism, from the genetic to the behaviour of the organism as a whole, as the most general characteristic of the organization of the living system.

Quantum biochemistry shows that the electronic structure of the macromolecules of the main compounds causes the dynamic nature of living matter through electronic delocalization.

This peculiarity of structure provides the living molecule with its great resistivity to ionizing radiations, and at the same time, the great polarizability, the mobility and the fluidity of the electron cloud of the conjugated molecule provide for the quick transmission of disturbances which, in the living body's biological language, can mean an order or a warning.

Recent research in biology and energizing medicine has revealed the existence of electromagnetic fields in living bodies and, in particular, the role they play in the slow system of control of the body, in determining the levels of functional activity in the body and in their relation with external electromagnetic micropulsations.

Research in biometeorology, in addition, has revealed the role played by electromagnetic fluctuations in the natural environment in the spectrum of low and very low frequencies of next-to-the-ground magnetic micropulsations in the behaviour of living beings. It can probably be assumed that such fluctuations have biological effects because they influence the characteristic information in the living body.

In this respect, it is therefore the object of the invention to propose a therapeutic method consisting in transmitting to a living substratum or body signals capable of having an effect on the informational organisation of the substratum in order to act on its functional behaviour to normalize or to dynamize it.

According to one main characteristic of the invention, each signal is constituted by a sequence of magnetic fields generated by selective couplings of homonymous (or like) and heteronymous (or different) magnetic poles define a wave or pulse train of selected form, which the said wave train is repeated at least three times. The signal frequency of the magnetic waves is of the order of 40 to 80 KHz, the pulse train duration is of the order of 100 to 200 microseconds, and the frequency of transmission varies between 1 and 600 pulse trains per second Hz. The strength of the magnetic field is limited to between 1 and 100 gauss, and the compatibility of the transmitted stimuli with the informational organization of the living organisms thus resides in the low power and low frequency (of the applied magnetic field).

In another aspect of the invention, successive pulses in the wave trains forming the signal are selectively applied to different magnetic poles, which results in a magnetic field having a different direction with each pulse. As a result, the signal has a dynamic form which experiments have shown to be significant and whose effect is related to the anisotropic character of the conjugated molecules of the living body from a magnetic standpoint.

Finally, the repetition of the alternations of the direction of the magnetic field gives the field a character which enables it to be differentiated by the organism from random or fortuitous signals.

A further object of the invention is to propose an apparatus for carrying the aforesaid method into effect, and comprising a transmission head provided with at least three non-aligned magnetic pole pieces, two of which are homonymous or like poles and one of which is heteronymous with respect to or different from the other two, the said poles being provided with coils adapted to be joined electrically into pairs and to be connected to an electric frequency generator, adjustable at between 40 and 80 KHz, by means of a filtration device for filtering the transmitted electric waves or pulses and to select only a predetermined number of them, adjustable so as to form a wave train, means for adjusting the time interval between the successive wave trains to provide them at between 1 and 600 trains per second, and pre-adjustable to logic or circuit means to ensure, in predetermined manner, the interconnection of like and different poles for each successive.

The invention will be more readily understood and secondary characteristics and advantages will emerge on reading the following description given by way of example and non-restrictively, reference being made to the accompanying drawings.

DETAILED DESCRIPTION OF ILLUSTRATIVE EMBODIMENTS

Figure 1:
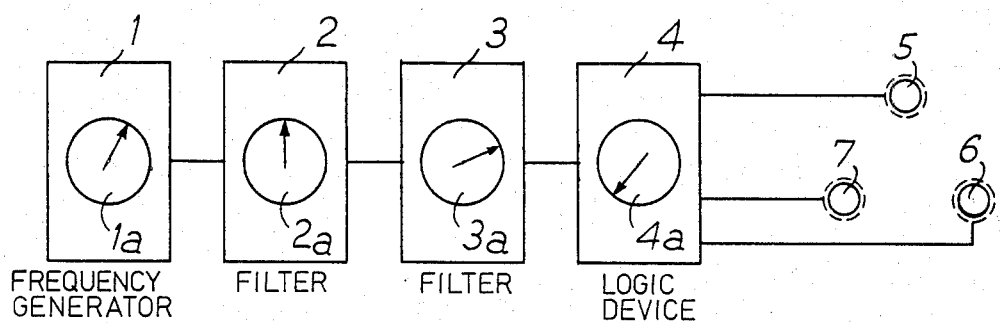
FIG. 1 diagrammatically illustrates an apparatus according to the invention.

Referring first to FIG. 1, there is seen a frequency generator 1, adapted to transmit a current whose frequency may be adjusted by 1a to between 40 and 80 KHz. Said current is directed into a device 2 for filtering a predetermined number of waves whose value may be displayed in 2a. The selected waves form wave trains issueing from the device 2 at a fixed frequency greater than 600 Hz. A second filtering device 3 makes it possible via 3a to control the time interval between the consecutive wave trains transmitted in output by the device 2 to between 1 and 600 trains per second. The arrangement described hereinabove is given by way of diagrammatical example and any known device with which the same result can be obtained remains within the scope of the invention. In the same way, it is possible, in known manner, to incorporate to the aforesaid unit, a device for converting each wave into a rectangular electrical signal.

Figure 6:
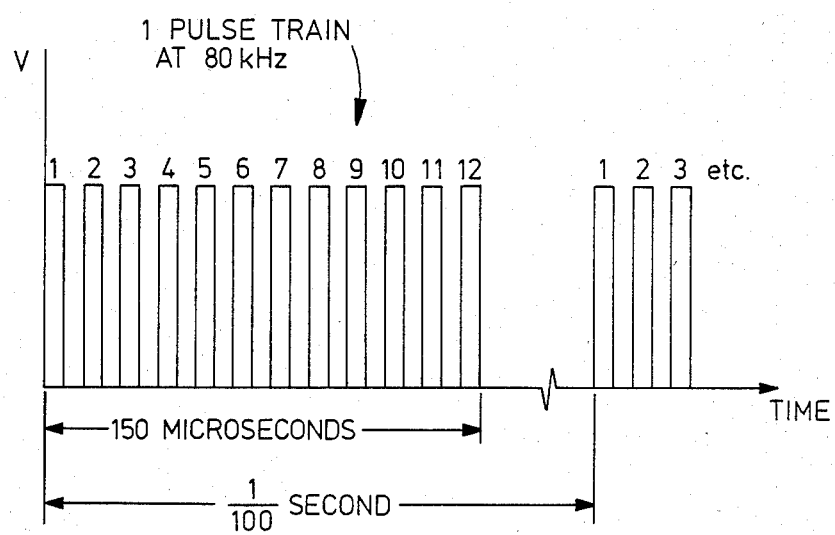
FIG. 6 illustrates the waveform of a series of pulse trains in accordance with the present invention.

Thus, wave trains (or rectangular pulse trains) are transmitted from the output of device 3, each train having a predetermined number of waves which follow one another at an equally predetermined frequency, and each train preceding the following one at an equally predetermined interval. For example, if a frequency of 80 KHz, is displayed by 1a, twelve waves by 2a, and a transmission frequency of 100 Hz or 100 pulse trains per second, by 3a then a succession of wave trains will be obtained at the output of apparatus 3, each of which comprises twelve waves (or rectangular pulses) running over 150 microseconds, each wave train being transmitted every hundredth of a second, as shown in FIG. 6.

Such a succession of wave trains is then directed towards pole pieces 5, 6 and 7 and more precisely into the coils thereof. These coils are such that, for example, pole pieces 5 and 7 are homonymous for example, both might be north magnetic poles, and piece 6 is a south magnetic pole and thus heteronymous with respect to the other two. A logical device 4 permits to produce the joining into pairs of the said coils according to a predetermined order by modifiable display (4a) in order that each successive wave of a wave or pulse train received at the input of the logical device, is directed to a different couple of pole pieces, so as to create a magnetic pulse the direction of which will depend of the homonymy or of the heteronymy of the coupled pieces.

If, for example, 4a displays the successive coupling of the coils of pieces 7 and 6, then of pieces 7 and 5 and of pieces 7 and 6, the first wave (1 in FIG. 6) of a wave train of twelve waves will cause the creation of a magnetic pulse running between pieces 7 and 6. The following wave (2 in FIG. 6) will cause a magnetic field between pieces 7 and 5, and since the pieces 7 and 5 are homonymous, said field will be running perpendicular to the plane containing them. The third wave (3 in FIG. 6) will create a pulse similar to that created by the first. This cycle will thus be repeated, at the passage of the three other groups (4, 5, 6; 7, 8, 9; 10, 11, 12) of three waves which the wave train is still carrying. The magnetic signal sent by the pole pieces is therefore constituted by four repetitions of a basic sub-signal the form of which is dependent on the couplings displayed by 4a in the logical device 3.

Figure 2:
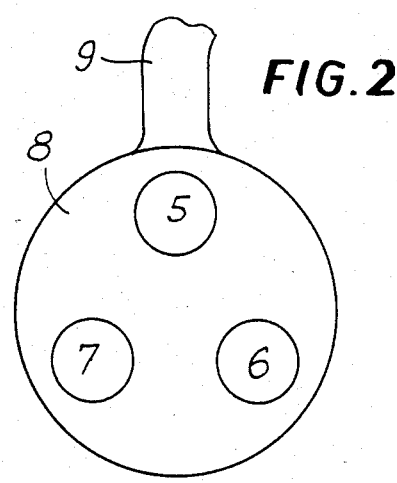
FIGS. 2 and 3 illustrate possible variants of a transmission head with three pole pieces.

The pole pieces 5, 6 and 7 are carried in non-aligned manner, by a transmission head 8 such as shown in FIG. 2. Said head may be plane or have any form (concave for example, such as shown in 8' in FIG. 3), and connected by a flexible cable 9 to the output of the apparatus bearing reference 1 to 4 in FIG. 1. It is clear that when the face of the head 8 which is visible in FIG. 2 is applied to the body of a patient, the magnetic pulses sent by pieces 5 and 7 extend into the living tissues, either substantially in parallel to the aforesaid face and therefore not deeply, or perpendicular thereto, and then more deeply, and this within a predetermined sequence repeated at least three times for one wave train, over a period varying between 100 and 200 microseconds and at a frequency equal to the frequency of succession of the wave trains.

It is of course possible to produce different couplings and in a different order. Thus, by coupling successively 6-5, then 5-7, and then 7-1, and this four times in succession, a signal is obtained which differs slightly from the signal previously described, in that the consecutive magnetic fields issued from the two homonymous poles are of different directions.

Figure 4:
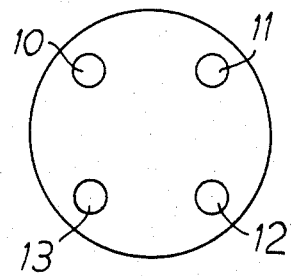

FIG. 4 diagrammatically shows a transmission head with four pole pieces 10, 11, 12, 13, situated at the top of a square of which 10, 11 and 12 are of similar polarity and 13 of reverse polarity. The experiments show that a signal issued from at least three repetitions of couplings 10-12, 11-13 is highly efficient.

Figure 5:
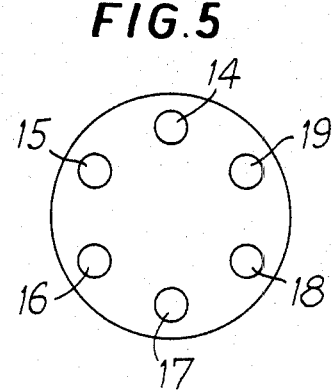
FIGS. 4 and 5 illustrate two further embodiments of transmission head.

Finally in FIG. 5, the pole pieces 14, 15, 16, 17, 18, 19 are placed at the top of a regular hexagon. Poles 16 and 18 which are not consecutive, have the same polarity and are of reverse polarity with respect to the four other poles. The experiments have shown that the most efficient signals which can be sent by such a head are issued from a repetition (at least three times), either of couplings 14-16-18, 15-17-19, or couplings 14-17, 15-18, 16-19. The head shown in FIG. 5 could advantageously be used—selecting only part of poles 14 to 19—as a three-poled head or as a four-poled head.

The three types of head described hereinabove constitute fundamental types; any type of head with more than six poles constitute a combination of these three types.

All the magnetic pulses sent when a wave train passes constitutes a signal of very precise form. Said signal is interpreted by the living body as one of its own internal signals, which it integrates into its informational organization. From that, there results modifications of a functional and biological nature in the body. Seeing that the geometrical form of the signal can be modified, by means of the displayed sequence of couplings, as well as its intensity and its frequency, significant combinations are thus obtained that determine the physiological action caused by the signal which potentially could help the natural processes of defence and perhaps cure the organism, as well as causing its functional readjustment.

Thus it was noted that with a signal according to the invention issued at a frequency of between 4 and 16 pulse trains per second and at low current, it is possible to increase the threshold of sensitivity of a patient (elimination of a localized pain). On the contrary, with a transmission frequency of between 400 and 600 Hz, and with a stronger current, nervous conduction is made easier and the defence reactions of the organism are dynamized. Finally, between 80 and 120 Hz with average power, the effect on the metabolic equilibration of the treated substratum is favorable.

The invention, by the fact that it uses signals (the magnetic strength being adjustable to between 1 and 100 gauss) with a low energy level, which it can be assumed have no direct physical action on the organism, causes no irreversible modification of the living substratum such as (anatomic destruction, or even disorganization of the regulating mechanisms). Its field of action lies in the fields of electronic biology and of biocybernetics, the signal issued being compatible with the signals of the informational organization of the body and having for the latter a biological significance.

The invention finds an application in the medical and paramedical fields.

It is not limited to the description given hereinabove but on the contrary covers any variants which may be made thereon, without departing from its scope or its spirit. For example, transmission heads may be provided which comprise a pluraality of pole pieces. Then the coupling of the heads should be such that the plane of two coupled homonymous heads crosses through the plane of two coupled heteronymous heads.

Figure 3:
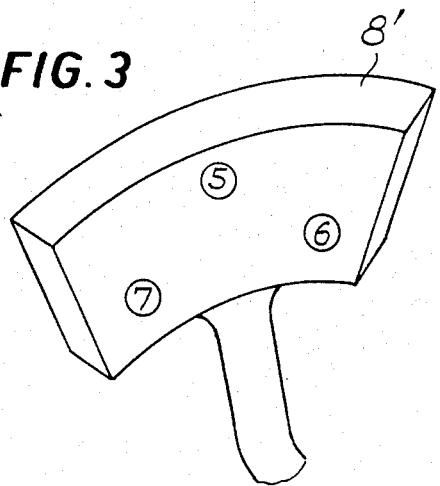

Also, a transmission head may be provided which is made either of flexible material so that it can adjust at least approximately to the outlines of the part to be treated—for example in the human body—or in two or more articulated parts, each part carrying poles adapted to be permanently coupled together (such as poles 10-12 and 11-13 of FIG. 3 or poles 14-16-18 and 15-17-19 of FIG. 6 for one type of coupling).

What is claimed is:

1. A method of treating living tissues by subjecting them to a magnetic field having a variable orientation produced by at least three electromagnetic means, the method comprising the steps of:
    providing an electrical signal comprising a plurality of pulse trains occurring at a transmission frequency of between 1 and 600 trains per second, each said pulse train including a plurality of electrical pulses occurring at a signal frequency of between 40 KHz and 80 KHz and each said pulse train having a duration of between 100 and 200 microseconds;
    selectively applying said pulses to said electromagnetic means to produce said magnetic field and change the orientation thereof with the occurrence of each said pulse; and
    limiting the strength of said magnetic field to between 1 and 100 gauss, whereby the living tissue interprets said magnetic field as an internal informational signal for altering its behavior and the magnetic field causes substantially no direct physical action on the living tissue.

2. A method as in claim 1; wherein said electromagnetic means comprise three electromagnetic devices, each said pulse is applied to two of said electromagnetic devices simultaneously, said pulses produce a magnetic field having a first orientation when applied to a first predetermined pair of said electromagnetic devices and another magnetic field having second orientation when applied to a second pair of electromagnetic devices, said first pair of electromagnetic devices have oppositely arranged magnetic poles and said second pair of electromagnetic devices have similarly arranged magnetic poles.

3. A method as in claim 1; wherein said signal frequency is approximately 80 KHz, each said pulse train has a duration of approximately 150 microseconds, said transmission frequency is approximately 100 pulse trains per second and said electrical signal includes at least three pulse trains.

4. A method as in claim 1 wherein said transmission frequency is between 4 and 16 pulse trains per second.

5. A method as in claim 1; wherein said transmission frequency is between 400 and 600 pulse trains per second.

6. A method as in claim 1; wherein said transmission frequency is between 80 and 120 pulse trains per second.

7. An apparatus for providing a magnetic field having an alternating orientation for treating living tissues, the apparatus comprising:
    signal generating means for generating an electrical signal having a signal frequency of between 40 KHz and 80 KHz;
    filtering means for providing said electrical signal as a series of pulse trains having a duration of between 100 and 200 microseconds;
    timing means for providing a time interval between said pulse trains wherein said pulse trains occur at a transmission frequency of between 1 and 600 pulse trains per second;
    an applicator head for providing a magnetic field and for application thereof to the living tissue, said head including at least three electromagnetic means being capable of oppositely arranged poles and similarily arranged poles for receiving said pulses; and
    circuit means for selectively applying each of said pulses to two said electromagnetic means simultaneously to produce said magnetic field having a first orientation when each said pulse is applied to a first predetermined pair of said electromagnetic means having oppositely arranged poles and a second orientation when applied to a second pair of said electromagnetic means having similarily arranged poles and for changing the orientation thereof with the occurrence of each said pulse and for limiting the strength of said magnetic field to between 1 and 100 gauss, whereby the living tissue interprets said magnetic field as an internal informational signal for altering its behavior and the magnetic field causes substantially no direct physical action on the living tissue.

8. An apparatus as in claim 7; wherein said electromagnetic means comprises three electromagnetic devices arranged in at least two pairs, a first pair of said electromagnetic devices having oppositely arranged poles and a second pair of said electromagnetic devices having similarly arranged poles, and said circuit means is arranged to alternately apply said pulses to said pairs for creating a magnetic field having a different orientation for each said pulse.

9. An apparatus as in claim 7; wherein said electromagnetic means comprises four electromagnetic devices, the first pair of electromagnetic devices including electromagnetic devices having oppositely arranged poles, the second pair of electromagnetic devices including electromagnetic devices having similarly arranged poles and said circuit means is arranged to alternately apply each of said pulses to each of said pairs for creating a magnetic field having a different orientation for each pulse.

10. An apparatus as in claim 9; wherein said applicator head has a planar face and said electromagnetic devices are disposed in said planar face.

* * * * *